(12) United States Patent
Fukuju et al.

(10) Patent No.: US 9,874,511 B2
(45) Date of Patent: Jan. 23, 2018

(54) ANALYZER AND IMMUNOASSAY METHOD

(71) Applicant: Sysmex Corporation, Kobe-shi, Hyogo (JP)

(72) Inventors: Toshikatsu Fukuju, Kobe (JP); Yusuke Matsumoto, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 214 days.

(21) Appl. No.: 14/669,801

(22) Filed: Mar. 26, 2015

(65) Prior Publication Data

US 2015/0276580 A1 Oct. 1, 2015

(30) Foreign Application Priority Data

Mar. 27, 2014 (JP) .................. 2014-066461

(51) Int. Cl.
| | |
|---|---|
| *G01N 35/02* | (2006.01) |
| *G01N 21/13* | (2006.01) |
| *G01N 21/75* | (2006.01) |
| *G01N 21/64* | (2006.01) |
| *G01N 35/00* | (2006.01) |
| *G01N 35/04* | (2006.01) |
| *G01N 35/10* | (2006.01) |

(52) U.S. Cl.
CPC ......... *G01N 21/13* (2013.01); *G01N 21/6428* (2013.01); *G01N 21/75* (2013.01); *G01N 35/0098* (2013.01); *G01N 35/04* (2013.01); *G01N 35/025* (2013.01); *G01N 2021/135* (2013.01); *G01N 2035/041* (2013.01); *G01N 2035/0406* (2013.01); *G01N 2035/103* (2013.01); *G01N 2201/022* (2013.01); *G01N 2201/025* (2013.01)

(58) Field of Classification Search
None
See application file for complete search history.

(56) References Cited

U.S. PATENT DOCUMENTS

| | | | |
|---|---|---|---|
| 5,147,529 A | 9/1992 | Lee et al. | |
| 2010/0110415 A1* | 5/2010 | Yamumoto | G01N 21/253 356/39 |

FOREIGN PATENT DOCUMENTS

| | | |
|---|---|---|
| JP | H02-161358 A | 6/1990 |
| JP | H05-119039 A | 5/1993 |
| JP | H6-148200 A | 5/1994 |
| JP | H8-94624 A | 4/1996 |
| JP | H8-178927 A | 7/1996 |
| JP | H9-49847 A | 2/1997 |
| JP | 2001-74749 A | 3/2001 |
| JP | 2001-91521 A | 4/2001 |
| JP | 2007-147659 A | 6/2007 |
| JP | 2008-89406 A | 4/2008 |
| JP | 2009-204386 A | 9/2009 |
| JP | 2011-012969 A | 1/2011 |
| JP | 2012-145449 A | 8/2012 |
| JP | 2013-145211 A | 7/2013 |
| WO | WO 2011/089966 A1 | 7/2011 |

\* cited by examiner

*Primary Examiner* — Rebecca L Martinez
(74) *Attorney, Agent, or Firm* — Brinks Gilson & Lione (57) ABSTRACT

An analyzer including a housing with a mutually adjacent first side and a second side, and an annular reagent holding part disposed within the housing is disclosed. An immunoassay method for measuring antigen or antibody of a measurement object contained in a sample and performed by the analyzer is also disclosed.

15 Claims, 6 Drawing Sheets

ANALYZER AND IMMUNOASSAY METHOD

RELATED APPLICATIONS

This application claims priority from prior Japanese Patent Application No. 2014-066461, filed on Mar. 27, 2014, entitled "ANALYZER", the entire contents of which are incorporated herein by reference.

BACKGROUND OF THE INVENTION

1. Field of the Invention

The present invention relates to an analyzer provided with a plurality of processing units, and an immunoassay method.

2. Description of the Related Art

Conventional analyzers which have a plurality of processing units are known (for example, refer to Japanese Patent Publication Application No. 2001-74749).

Japanese Patent Publication Application No. 2001-74749 discloses an analyzer provided with a plurality of processing units and annular turntable. A plurality of cuvettes are disposed around the circumference of the turntable, and the cuvettes are moved in the circumferential direction of the turntable in conjunction with the rotation of the turntable. The turntable also functions as a reactor in which samples contained in the cuvettes are heated to induce a reaction. The plurality of processing units are arranged around the circumference of the turntable in the direction of movement of the cuvettes. In this analyzer, samples are analyzed by sequentially moving the cuvettes sequentially to the position at which each of the processing units is installed in conjunction with the rotation of the turntable, and performing predetermined processing of the sample in the respective cuvettes.

In Japanese Patent Publication Application No. 2001-74749, however, the plurality of processing units must be arranged along the direction of movement of the cuvette (circumferential direction) in the order of processing. In Patent Document 1, therefore, there is plentiful dead space between the plurality of processing units since the plurality of processing units must be arranged circularly around the circumference of the annular turntable. As a result a problem arises in the analyzer due to the increase in installation area which enlarges the analyzer in the horizontal direction.

SUMMARY OF THE INVENTION

The scope of the present invention is defined solely by the appended claims, and is not affected to any degree by the statements within this summary.

One aspect of the present invention is an analyzer provided with a housing which has a mutually adjacent first side and a second side; an annular reagent holding part provided within the housing; a first cuvette transporting part configured to move a cuvette, provided along the first side of the housing on the periphery of the reagent holding part; a second cuvette transporting part configured to move a cuvette, provided along the second side of the housing on the periphery of the reagent holding part; and a plurality of processing units respectively arranged in either a first direction extending along the first side or a second direction extending along the second side in planar view, and configured to receive a cuvette which is moved by the first cuvette transporting part or the second cuvette transporting part, and perform predetermined processing of the sample contained in the received cuvette.

Second aspect of the present invention is an analyzer provided with a housing which has a mutually adjacent first side and a second side; an annular reagent holding part provided within the housing; a first cuvette transporting part configured to move a cuvette, provided along the first side of the housing on the periphery of the reagent holding part; a second cuvette transporting part configured to move a cuvette, provided along the second side of the housing on the periphery of the reagent holding part; and a plurality of processing units respectively arranged in either a first direction extending along the first side or a second direction extending along the second side in planar view, and configured to receive a cuvette which is moved by the first cuvette transporting part or the second cuvette transporting part, and perform predetermined processing of the sample contained in the received cuvette; wherein the first cuvette transporting part comprises a first holding part capable of holding a cuvette, and is configured to reciprocatingly move the first holding part in the first direction; at least one of the plurality of processing units is a reaction unit arranged along the first side, and configured to hold a cuvette in which a sample reaction occurs; at least one of the plurality of processing units is a BF separator arranged along the first side, and configured to separate the unreacted components in the sample contained in the cuvette; the first cuvette transporting part is configured to move the cuvette from the reaction unit to the BF separator; the BF separator is configured to separate the unreacted components in the sample contained in the cuvette received from the reaction unit; and the first cuvette transporting part is configured to move the cuvette from which the unreacted components have been separated by the BF separator to the reaction unit.

Third aspect of the present invention is an immunoassay method for measuring antigen or antibody of a measurement object contained in a sample and performed by an analyzer comprising a housing with a mutually adjacent first side and a second side, and an annular reagent holding part disposed within the housing, the method comprising: binding a magnetic particle to the measurement object in the sample contained in a cuvette using a reaction unit arranged along the first side; moving the cuvette from the reaction unit to a BF separator arranged along the first side; separating the unreacted components in the sample contained in the cuvette received from the reaction unit in the BF separator; dispensing a labeling substance to the cuvette from which the unreacted components have been removed by the BF separator; moving the cuvette containing the dispensed labeling substance to the reaction unit; and measuring the measurement object based on the labeling substance in a complex comprising the labeling substance, the measurement object, and the magnetic particle after the complex has been formed in the cuvette moved to the reaction unit through an antigen-antibody reaction.

DETAILED DESCRIPTION OF THE PREFERRED EMBODIMENTS

The embodiments of the present invention are described below based on the drawings.

The structure of the analyzer 100 of an embodiment of the present invention is described below with reference to FIGS. 1 through 4. The analyzer 100 is an immunological analyzer which measures a measurement object such as antigen or antibody contained in a sample to be measured. The sample is a blood sample such as serum.

The measurement operation is summarized below. The analyzer 100 binds a capture antibody to an antigen contained in the sample by and antigen-antibody reaction, then binds magnetic particles to the capture antibody which is bound to the antigen. The analyzer 100 then performs a primary BF separation process to remove the unreacted capture antibody by collecting the complex containing the bound antigen, the capture antibody, and the magnetic particles via magnetic force. After the labeling antibody is bound to the complex as a labeling substance, the analyzer 100 performs a secondary BF separation process to remove the unreacted labeling antibody by collecting the complex which contains the bound magnetic particles, antigen, and labeling antibody via magnetic force. After a dispersion liquid and luminescent substrate have been added, the analyzer 100 then measures the amount of luminescence produced by the reaction between the labeling antibody and the luminescent substrate. The analyzer 100 is configured to perform sample analyses according to a plurality of different analysis items by quantitatively measuring the antigen bound to the labeling antibody through this process. The capture antibody, magnetic particles, labeling antibody, dispersion liquid, and luminescent substrate added to the measurement sample are hereinafter respectively referred to as R1 reagent, R2 reagent, R3 reagent, R4 reagent, and R5 reagent.

Figure 1:
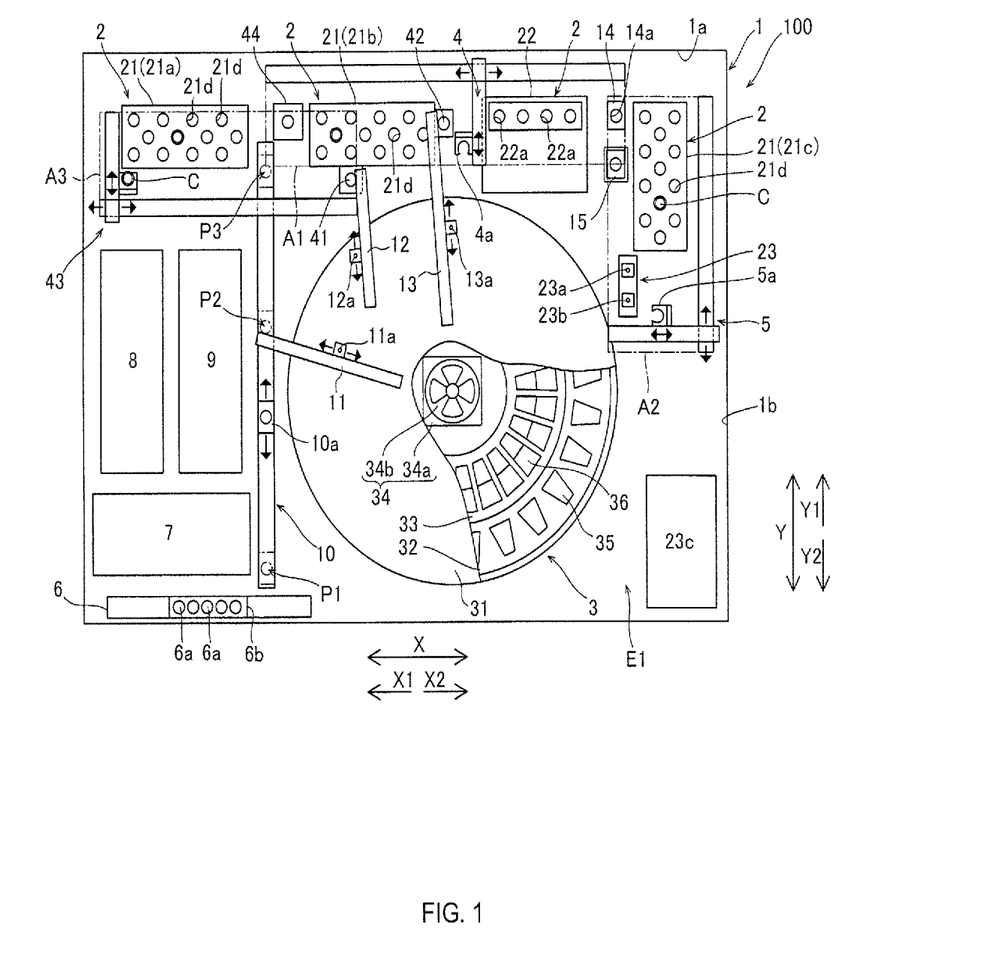
FIG. 1 is a schematic plan view showing the structure of the first stage of the analyzer of an embodiment of the invention.

As shown in FIG. 1, the analyzer 100 is configured by a housing 1, a plurality of processing units 2, reagent holding part 3, first cuvette transporting part 4, and second cuvette transporting part 5. The analyzer 100 also is provided with a sample mover 6, sample dispenser 7, tip supplier 8, cuvette supplier 9, sample dispensing cuvette mover 10, a plurality of reagent dispensers 11, 12, and 13, relay part 14, interstage transporting part 15, and elevator device 16 (refer to FIG. 2). The analyzer 100 also is provided with a controller 17 (refer to FIG. 2) to control the various parts.

The housing 1 is rectangular in shape in planar view, and includes a mutually adjacent first side 1a in the longitudinal direction and a second side 1b in the lateral direction. That is, the housing 1 has a box-like shape which is substantially rectangular. The housing 1 internally houses the various parts of the analyzer 100 such as the plurality of processing units 2. Note that the first side 1a and the second side 1b respectively indicate the inside surfaces of the housing 1. The first side 1a and the second side 1b are flat surfaces extending in a first direction and a second direction in planar view. Note that hereinafter the first direction which is the horizontal direction along the first side 1a is designated the X direction, the second direction which is the horizontal direction along the second side 1b is designated the Y direction, and the vertical direction which intersects the first direction and the second direction is designated the Z direction. The housing 1 need not necessarily be rectangular in shape, inasmuch as the housing 1 also may be, for example, square in shape.

The housing 1 incorporates a first stage E1 and a second stage E2 (refer to FIG. 2) which differs in a vertical direction from the first stage E1. That is, the housing 1 has a hierarchical structure having a plurality of stages in vertical directions. The reagent holding part 3, first cuvette transporting part 4, second cuvette transporting part 5, an a plurality of processing units 2 are arranged in the first stage E1 of the upper level. Note that the housing 1 may be configured by only a single stage, or may be configured by three or more stages.

Figure 2:
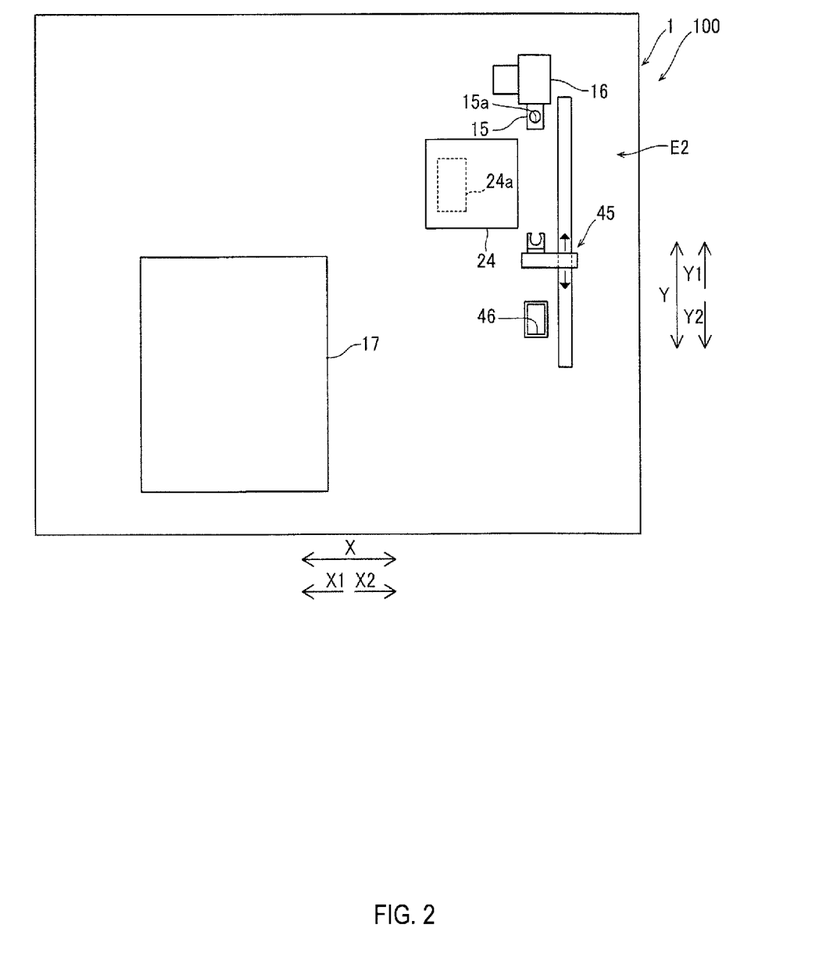
FIG. 2 is a schematic plan view showing the structure of the second stage of the analyzer of the embodiment of the invention.

The plurality of processing units 2 are configured to respectively receive the reaction container cuvette moved by the first cuvette transporting part 4 or the second cuvette transporting part 5, and perform predetermined processing of the sample contained in the received cuvette. Among the plurality of processing units 2 arranged in the first stage E1, at least some processing units are arranged along the direction (first direction) extending along the first side 1a, and some other processing units are arranged along the direction (second direction) extending along the second side 1b. A plurality of processing units 2 related to sample preparation are disposed in the first stage E1. The plurality of processing units 2 in the first stage E1 are arranged around the annular reagent holding part 3. Among the plurality of processing units 2 arranged in the second stage E2 of the housing 1, the processing units 2 differ from the processing units 2 arranged along the first side 1a of the first stage E1 and the processing units 2 arranged along the second side 1b of the first stage E1, as shown in FIG. 2. Processing units 2 related to performing measurements of the measurement sample are arranged in the second stage E2.

More specifically, the plurality of processing units 2 include a plurality of reactors 21, one BF separator 22, R4/R5 reagent dispensers 23, and detector 24 (refer to FIG. 2). There are three reactors 21 in the present embodiment. The three reactors 21 are identified as first reactor 21a, second reactor 21b, and third reactor 21c below for convenience. Note that the reactors 21 also may be one, two, four or more in number. Among the plurality of processing units 2, the first reactor 21a, second reactor 21b, and BF separator 22 are aligned in the first direction X along the first side 1a in the longitudinal direction. Among the plurality of processing units 2, the third reactor 21c, and R4/R5 reagent dispensers 23 are aligned in the second direction Y along the second side 1b in the lateral direction. These processing units 2 are arranged in the first stage E1. As shown in FIG. 2, the detector 24 among the plurality of processing units 2 is arranged in the second stage E2. The specific structures of each processing unit 2 is described later. Note that other processing units may be included among the plurality of processing units 2. Examples of such other processing units include R2 dispensing port 41, R3 dispensing port 42, and magnet collecting port 44 configured to receive a cuvette moved by the first cuvette transporting part 4 or the second cuvette transporting part 5. The BF separator and detector also may be provided in plurality.

As shown in FIG. 1, the reagent holding part 3 has an annular shape in planar view, and is provided within the housing 1. The reagent holding part 3 is arranged near the center of the housing 1 in planar view. The reagent holding part 3 includes a cylindrical case 31, annular reagent receiving parts 32 and 33, and a cooling device 34.

The case 31 internally houses the reagent receiving parts 32 and 33, and the cooling device 34, and heat transfer is blocked between the inside and outside of the case 31 by a heat shield wall. The annular reagent receiving parts 32 and 33 are arranged concentrically, and are configured to be mutually independently rotatable. Reagent containers 35 containing R2 reagent are aligned in plurality along the ring in the outer reagent receiving part 32. Reagent containers 36 containing R1 reagent and R3 reagent are aligned in plurality along the ring in the inner reagent receiving part 33. Note that the reagent containers 36 are divided into two sections with each having a reagent accommodating empty space within, and hold R1 reagent and R3 reagent, respectively. A plurality of reagent containers 35 and 36 are positioned at predetermined reagent aspirating positions via the rotation of the reagent receiving parts 32 and 33.

The cooling device 34 also includes a cooling element 34a such as a Peltier element, and a fan 34b for circulation. The reagent holding part 3 is thus configured to internally house and cool a plurality of reagent containers 35. Note that three aspiration ports (not shown in the drawing) which can be opened and closed are provided on the top surface of the case 31 to aspirate the R1, R2, and R3 reagents, respectively.

The first cuvette transporting part 4 and the second cuvette transporting part 5 have the function of respectively moving the cuvette C. The first cuvette transporting part 4 in the first embodiment is provided along the first side 1a of the housing 1 on the periphery of the reagent holding part 3. The second cuvette transporting part 5 is provided along the second side 1b of the housing 1 on the periphery of the reagent holding part 3. The first cuvette transporting part 4 and the second cuvette transporting part 5 are arranged on the outermost side of the plurality of processing units within the housing 1. The first cuvette transporting part 4 and the second cuvette transporting part 5 also are arranged around the annular reagent holding part 3.

Figure 3:
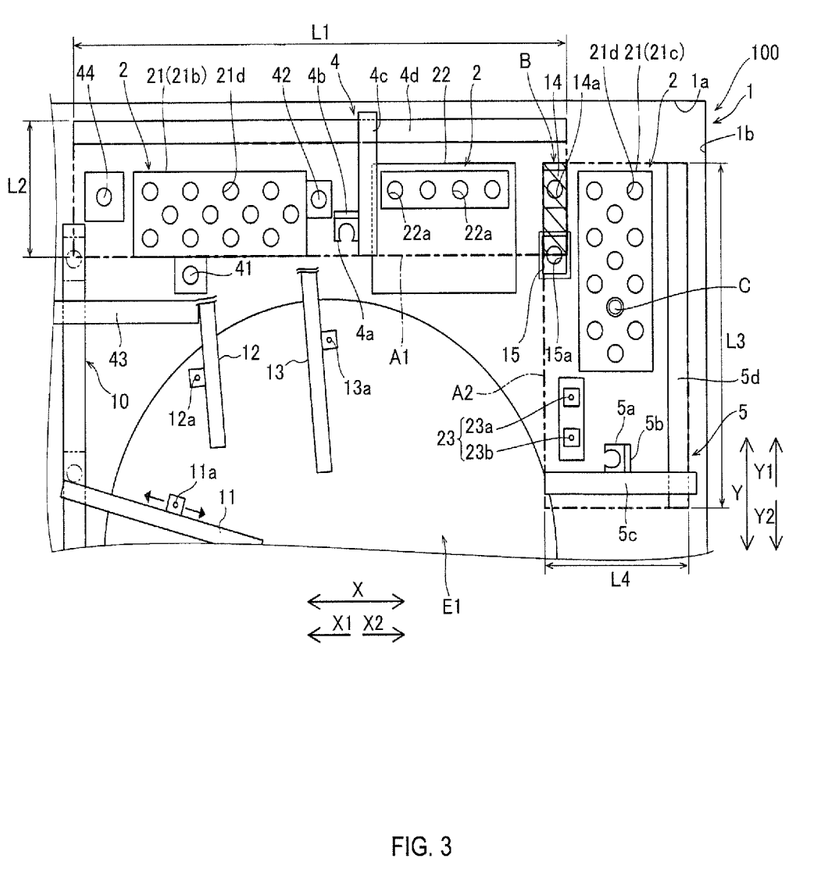
FIG. 3 is a partial enlargement illustrating the respective transporting regions of the first cuvette transporting part and the second cuvette transporting part.

As shown in FIG. 3, the first cuvette transporting part 4 incorporates a first holder 4a capable of holding a cuvette C, a first rail 4b which supports the first holder 4a so as to be linearly movable in the vertical direction Z, a second rail 4c which supports the first rail 4b so as to be linearly movable in the second direction Y, and a third rail 4d which supports the second rail 4c so as to be linearly movable in the first direction X. The first cuvette transporting part 4 is configured to move the first holder 4a back and forth in the first direction X, second direction Y, and vertical direction Z along the first side 1a via the drive of three motors (not shown in the drawing) for moving in the various directions. The first cuvette transporting part 4 therefore holds the cuvette C one by one and moves the cuvette C to the processing unit 2 via the first holder 4a. The first cuvette transporting part 4 also is configured to move the cuvette C to the relay part 14 after processing is completed by the processing units 2 arranged along the first side 1a.

The movement range of the first holder 4a is regulated by the first rail 4b, second rail 4c, and third rail 4d. In the horizontal direction, the first cuvette transporting part 4 can move the first holder 4a within the movement range defined by the movement range L1 in the first direction X and the movement range L2 in the second direction Y. Accordingly, the movable range A1 of the cuvette C by the first cuvette transporting part 4 is a rectangular region which has the movement range L1 in the first direction X and the movement range L2 in the second direction Y on the sides of the rectangular area. In this case, the movement range L1 of the first holder 4a in the first direction X is configured to be greater than the movement range L2 in the second direction Y. The first cuvette transporting part 4 therefore has a long and narrow range of movement A1 with the first direction X along the first side 1a as the longitudinal direction between the first side 1a and the reagent holding part 3.

The second cuvette transporting part 5 incorporates a second holder 5a capable of holding a cuvette C, a first rail 5b which supports the second holder 5a so as to be linearly movable in the vertical direction Z, a second rail 5c which supports the first rail 5b so as to be linearly movable in the first direction, and a third rail 5d which supports the second rail 5c so as to be linearly movable in the second direction X. The second cuvette transporting part 5 is configured to move the second holder 5a back and forth in the second direction Y, first direction X, and vertical direction Z along the second side 1b via the drive of three motors (not shown in the drawing) for moving in the various directions. The second cuvette transporting part 5 therefore holds the cuvette C one by one and moves the cuvette C to the processing unit 2 via the second holder 5a. The second cuvette transporting part 5 is configured to move the cuvette C in the relay part 14 to the processing unit 2 arranged along the second side 1b.

In the horizontal direction, the second cuvette transporting part 5 can move the second holder 5a within the range defined by the moving range L3 in the second direction and the movement range L4 in the first direction X. The movable range A2 of the second cuvette transporting part 5 is a rectangular region which has the movement range L3 in the second direction Y and the movement range L4 in the first direction X on the sides of the rectangular area. The movement range L3 of the second holder 5a in the second direction Y is configured to be greater than the movement range L4 in the first direction X. The second cuvette transporting part 5 therefore has a long and narrow range of movement A2 with the second direction Y along the second side 1b as the longitudinal direction between the second side 1b and the reagent holding part 3.

In the present embodiment, the first cuvette transporting part 4 and the second cuvette transporting part 5 are configured to have partially mutually overlapping cuvette C transport regions in planar view. That is, the movement region A1 of the first cuvette transporting part 4 and the movement region A2 of the second cuvette transporting part 5 overlap in the overlap area B indicated by the hatch marks in FIG. 3. Note that among the plurality of processing units, the transport position of the cuvette C to the processing units 2 disposed along the first side 1a is arranged to be within the moving range L1×L2 of the first holder 4a. That is, the plurality of cuvette retaining holes 21d (described later) of the second reactor 21b, and the plurality of processing ports 22a (described later) of the BF separator 22 are respectively arranged within the moving range A1. Among the plurality of processing units 2, the transport position of the cuvette C to the processing units 2 disposed along the second side 1b is arranged to be within the moving range L3×L4 of the second holder 5a. That is, the plurality of cuvette retaining holes 21d of the third reactor 21c, and the R4 reagent nozzle 23a and the R5 reagent nozzle 23b (described later) of the R4/R5 reagent dispenser 23 are respectively arranged within the moving range A2.

Note that the first cuvette transporting part 4 and the second cuvette transporting part 5 also may be provided in plurality. For example, a plurality of first cuvette transporting parts 4 may be provided on a shared third rail 4d. The first cuvette transporting part 4 also may be exclusively provided for transport between a specific plurality of processing units 2. For example, a first cuvette transport part may be provided for transport between the second reactor 21b and the BF separator 22, and a first cuvette transporting part also may be provided for transport between the BF separator 22 and the relay part 14. The second cuvette transporting part may be similarly configured.

As shown in FIG. 1, the sample mover 6 transports a rack 6b loaded with a plurality of test tubes 6a containing sample to a predetermined sample aspirating position. The sample dispenser 7 is configured to aspirate the sample in the test tube 6a, and dispense the aspirated sample into a cuvette C disposed at the sample dispensing position P1. Note that the sample dispenser 7 is configured so that a disposable pipette tip (not shown in the drawing) supplied by the tip supplier 8 can be mounted thereon for dispensing sample.

The sample dispensing cuvette mover 10 is provided the direction (second direction Y) extending along the second side 1b. The sample dispensing cuvette mover 10 is provided to circumscribe the plurality of processing units 2 and the annular reagent holding part 3. The sample dispensing cuvette mover 10 incorporates a sample dispensing cuvette holder 10a which holds the cuvette C and is movable in the second direction. When the cuvette C is supplied from the cuvette supplier 9 to the sample dispensing cuvette holder 10a, the sample dispensing cuvette mover 10 transports the received cuvette C to the sample dispensing position P1, R1 reagent dispensing position P2, and cuvette removal position P3.

The plurality of reagent dispensers 11, 12, and 13 are respectively configured to linearly move the pipettes 11a, 12a, and 13a used to aspirate and discharge reagent between the reagent aspirating position and the reagent dispensing position. The pipette 11a of the reagent dispenser 11 aspirates the R1 reagent from the reagent container 36 through an aspirating port (not shown in the drawing) of the reagent holding part 3, and dispenses the aspirated R1 reagent into the cuvette C disposed at the R1 reagent dispensing position P2. The pipette 12a of the reagent dispenser 12 aspirates the R2 reagent from the reagent container 35 of the reagent holding part 3, and dispenses the aspirated R2 reagent into the cuvette C disposed at the R2 reagent dispensing position 41. The pipette 13a of the reagent dispenser 13 aspirates the R3 reagent from the reagent container 36 of the reagent holding part 3, and dispenses the aspirated R3 reagent into the cuvette C disposed at the R3 reagent dispensing position 42.

The three reactors 21 have mutually identical structures in common. That is, the three reactors 21 have a rectangular shape in planar view in common. The three reactors 21 also are configured to hold the cuvette C and induce the reaction of the sample contained in the cuvette C. Specifically, the three reactors 21 respectively have a plurality of cuvette retaining holes 21d, and are configured to heat the sample contained in the cuvette C set in the cuvette retaining hole 21d.

Among the three reactors 21, the first reactor 21a is positioned within the housing 1 near the corner at which the X1 direction side meets the Y1 direction side. The first reactor 21a is arranged at a position separated from the reagent holding part 3 so as to sandwich the sample dispensing cuvette mover 10 therebetween in the center part within the housing 1. The first reactor 21a performs a first order reaction process of the sample in the cuvette C after the sample and R1 reagent dispensing operations, and performs a secondary reaction process of the same sample after the R2 reagent dispensing operation. An upstream cuvette mover 43 is provided near the first reactors 21a. The upstream cuvette mover 43 transports the cuvette C between the cuvette removal position P3, the first reactor 21a, magnet port 44 (described later), and R2 reagent dispensing port 41.

The magnet port 44 capable of holding the cuvette C is provided at a position between the first reactor 21a and the second reactor 21b. The magnet port 44 has an internal permanent magnet which is not shown in the drawing, and has the function of collecting the magnetic particles in the cuvette positioned at the magnet port 44. The magnet port 44 also is disposed in the overlap area of the transporting region A3 of the upstream cuvette mover 43 and the transporting region A1 of the first cuvette moving part 4. The cuvette C therefore can pass between the first cuvette moving part 4 and the upstream cuvette mover 43. Note that although the upstream cuvette mover 43 is provided in the present embodiment, the first cuvette moving part 4 also may perform the transport operation of the upstream cuvette mover 43 instead of providing the upstream cuvette mover 43. That is, the third rail 4d may be extended to near the end of the housing 1 on the side in X1 direction, and the first cuvette moving part 4 may be configured to cover the transporting region A3 of the upstream cuvette mover 43.

The second reactor 21b is arranged at a position near the first side 1a in the center of the housing 1 in the first direction X. The second reactor 21b is arranged at a position separated from the reagent holding part 3 within the transport region A1 of the cuvette C moved by the first cuvette transporting part 4. The second reactor 21b is separated from reagent holding part 3 so as to sandwich the R2 dispensing port 41 provided in the Y2 direction side. The R3 dispensing port 42 is arranged between the second reactor 21b and the BF separator 22. The second reactor 21b performs the third order reaction process on the sample after the R3 reagent has been dispensed. Note that the first reactor 21a and the second reactor 21b are arranged with the longitudinal direction facing the first direction X along the first side 1a.

The BF separator 22 is arranged at a position near the first side 1a between the second reactor 21b and the third reactor 21c. The BF separator 22 is configured to perform a BF separation process to separate the unreacted component in the sample contained in the cuvette C. The BF separator 22 incorporates several processing ports 22a which respectively accommodate a cuvette C. Four processing ports 22a are provided in the present embodiment. The four processing ports 22a are aligned along the first direction X, and the first cuvette transporting part 4 individually moves the cuvette C to the respective processing ports 22a. Note that the BF separator 22 is configured to perform both the primary BF separation process and the secondary BF separation process. Among the four processing ports 22a, the first cuvette transporting part 4 is configured to move the cuvette C to the processing port 22a nearest the destination side of the cuvette C after the BF separation process. Specifically, after the BF separation process, the cuvette C is moved to the second reactor 21b after R3 reagent has been dispensed. After the BF separation process, the cuvette C also is moved through the relay part 14 to the third reactor 21c after the R4 and R5 reagents have been dispensed. The cuvette C therefore is moved to one of the processing ports 22a on the X1 direction side near the second reactor 21b during the primary BF separation process, and the cuvette C is moved to one of the processing ports 22a on the X2 direction side near the third reactor 21c and relay part 14 during the secondary BF separation process. The BF separator 22 is configured to simultaneously perform the primary BF separation process on two cuvettes C, and the secondary BF separation process on two cuvettes C via the four processing ports 22a.

As shown in FIG. 3, the relay part 14 is arranged in the overlap area B of the transport region A1 of the first cuvette transporting part 4 and the transport region A2 of the second cuvette transporting part 5. The relay part 14 is configured to retain the cuvette C in a cuvette retainer 14a. The cuvette C is moved to the relay part 14 after the secondary BF separation process. In the relay part 14, the cuvette C is passed between the first cuvette transporting part 4 and the second cuvette transporting part 5. Note that the relay part 14 also may be omitted. For example, instead of providing the relay part 14, the transport region A2 of the second cuvette transporting part 5 may be extended to the BF separator 22 so that the second cuvette transporting part 5 can take up the cuvette C after the secondary BF separation process.

As shown in FIG. 1, the R4/R5 reagent dispenser 23 is arranged at a position near the second side 1n between the third reactor 21c and the reagent holding part 3. The R4/R5 reagent dispenser 23 has an R4 reagent nozzle 23a and an R5 reagent nozzle 23b respectively connected to an R4 reagent container (not shown in the drawing) and R5 reagent container (not shown in the drawing) housed in the container housing 23c. The R4 reagent nozzle 23a and R5 reagent nozzle 23b are configured to respectively discharge R4 reagent and R5 reagent into the cuvette C when the cuvette C is disposed at a position below the R4 reagent nozzle 23a and R5 reagent nozzle 23b by the second cuvette transporting part 5.

The cuvette C is moved to the third reactor 21c after the R4 reagent and R5 reagent have been dispensed to the cuvette C. The third reactor 21c is positioned within the housing 1 near the corner at which the X2 direction side meets the Y1 direction side. The third reactor 21c is arranged with the longitudinal direction facing the second direction Y along the second side 1b. The second reactor 21b is arranged at a position separated from the reagent holding part 3 within the transport region A2 of the cuvette C moved by the second cuvette transporting part 5. The third reactor 21c is separated from reagent holding part 3 so as to sandwich the R4/R5 reagent dispenser 23 therebetween.

Figure 4:
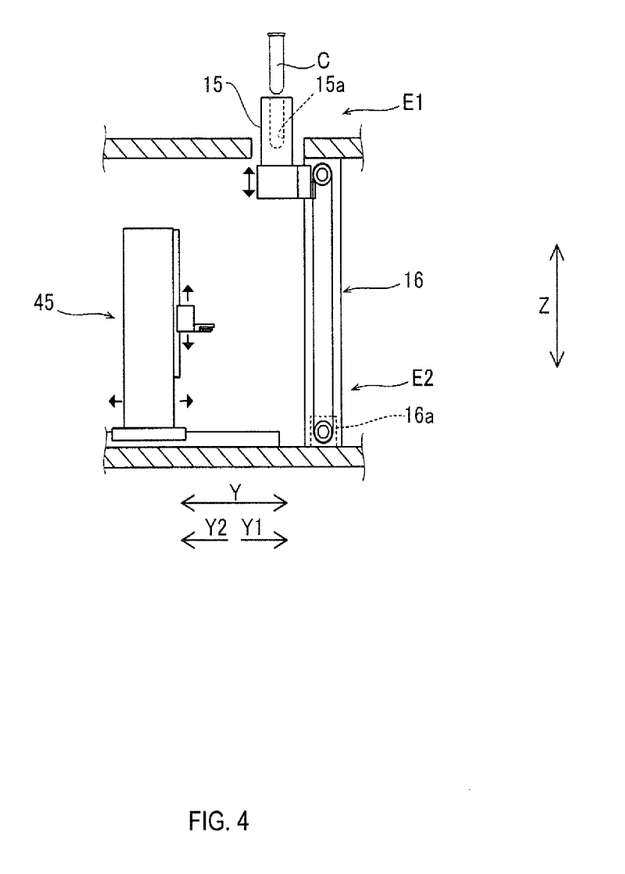
FIG. 4 is a schematic longitudinal section view showing the interstage transporting part and the elevator device of the analyzer of the embodiment of the invention.

The interstage transporting part 15 is provided at a position within the transport region A2 in the first stage E1. As shown in FIG. 4, the interstage transporting part 15 is configured to retain the cuvette C in the cuvette retainer 15a. The elevator device 16 is provided in the second stage E2, and is configured to move the cuvette C between the first stage E1 and the second stage E2 by lifting and lowering the interstage transporting part 15. The elevator device 16 also is configured to linearly move the interstage transporting part 15 in the vertical direction Z. Note that the interstage transporting part 15 also may be provided at a position within the second stage E2.

As shown in FIG. 2, the detector 24, elevator device 16, third cuvette transporting part 45, cuvette disposal port 46, and controller 17 are arranged in the second stage E2 of the housing 1. The third cuvette transporting part 45 is configured to move the cuvette C between the interstage transporting part 15 when lowered to the second stage E2, detector 24, and cuvette disposal port 46.

The detector 24 incorporates an optical detector 24a such as a photomultiplier. The detector 24 measures the amount of antigen contained in the sample by using the photomultiplier 24a to obtain the light generated in the reaction process between the luminescent substrate and the labeled antibody bound to the antigen of the sample which has been subjected to predetermined processing.

The controller 17 is configured by a PC (personal computer) which includes a CPU and memory unit not shown in the drawing. The PC functions as the controller of the analyzer 100 when the CPU executes a control program stored in the memory unit. The controller 17 controls the operation of the various parts, such as the plurality of processing units 2, first cuvette transporting part 4, and second cuvette transporting part 5.

The measurement process of the analyzer 100 is described below with reference to FIGS. 1, 2, and 5. Note that the operation control of the analyzer 100 is performed by the controller 17 (refer to FIG. 2). Although in practice the processing operations of each sample in a plurality of cuvettes C are performed in parallel, only the analysis process of a sample in a single cuvette C is described below.

Figure 5:
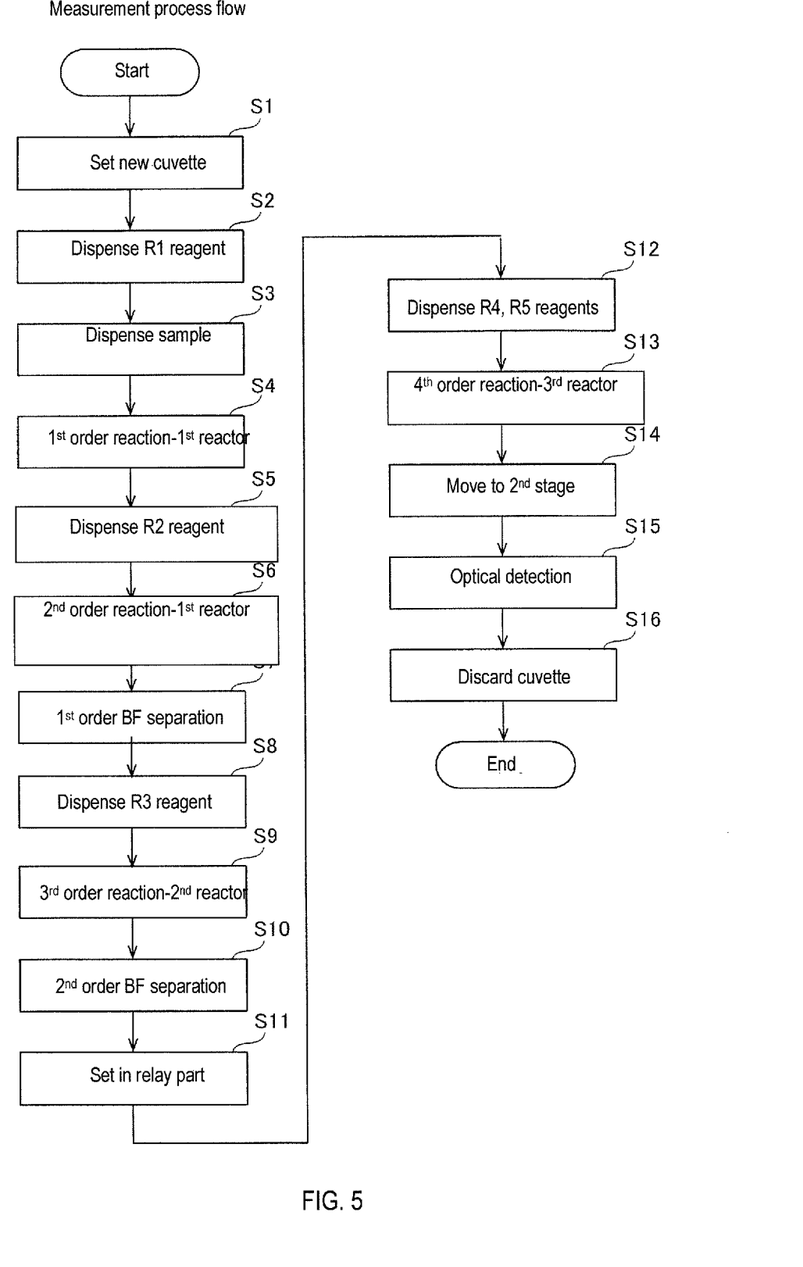
FIG. 5 is a flow chart illustrating the measurement process of the analyzer of the embodiment of the invention.

In step S1 of FIG. 5, a new cuvette C is supplied from the cuvette supplier 9 and set in the sample dispensing cuvette mover 10, as shown in FIG. 1. In step S2, the sample dispensing cuvette mover 10 moves the cuvette C to the R1 reagent dispensing position P2, and the reagent dispenser 11 dispenses the R1 reagent aspirated from the reagent container 36 into the cuvette C. In step S3, the sample dispensing cuvette mover 10 moves the cuvette C to the sample dispensing position P1, and the sample dispenser 7 dispenses the sample aspirated from the test tube 6a into the cuvette C.

In step S4, the sample dispensing cuvette mover 10 moves the cuvette C to the cuvette removal position P3, and the upstream cuvette mover 43 takes up the cuvette C and sets the cuvette C in the cuvette retaining hole 21d of the first reactor 21a. In this condition, the sample and R1 reagent within the cuvette C is subjected to a first order reaction process by heating to a predetermined temperature for a predetermined time.

In step S5, the upstream cuvette mover 43 moves the cuvette C from the first reactor 21a to the R2 reagent dispensing port 41, and the reagent dispenser 12 dispenses the R2 reagent aspirated from the reagent container 35 into the cuvette C.

In step S6, the upstream cuvette mover 43 removes the cuvette C from the R2 dispensing port 41, and sets the cuvette C in the cuvette retaining hole 21d of the first reactor 21a. In this condition, the sample, R1 reagent, and R2 reagent within the cuvette C is subjected to a second order reaction process by heating to a predetermined temperature for a predetermined time.

Then the primary BF separation process is performed in step S7. Specifically, the upstream cuvette mover 43 moves the cuvette C from the first reactor 21a to the magnet port 44. The magnetic particle in the cuvette C are collected via magnetic force when the cuvette C is moved to the magnet port 44. The first cuvette transporting part 4 then moves the cuvette C from the magnet port 44 to the BF separator 22. At this time the cuvette C is set at one of the processing ports 22a on the X1 direction side. The BF separator 22 then collects the complex which includes the antigen, R1 reagent, and R2 reagent within the cuvette C via magnetic force, and removes the unreacted R1 reagent.

In step S8, the first cuvette transporting part 4 moves the cuvette C from the BF separator 22 to the R3 reagent dispensing port 42, and the reagent dispenser 13 dispenses the R3 reagent aspirated from the reagent container 36 into the cuvette C.

In step S9, the first cuvette transporting part 4 removes the cuvette C from the R3 dispensing port 42, and sets the cuvette C in the cuvette retaining hole 21*d* of the second reactor 21*b*. In this condition, the sample, R1 reagent, R2 reagent, and R3 reagent within the cuvette C is subjected to a third order reaction process by heating to a predetermined temperature for a predetermined time.

Then the secondary BF separation process is performed in step S10. Specifically, the first cuvette transporting part 4 moves the cuvette C from the second reactor 21*b* to the magnet port 44, and the magnetic particles within the cuvette C are collected. The first cuvette transporting part 4 then moves the cuvette C from the magnet port 44 to the BF separator 22. At this time the cuvette C is set at one of the processing ports 22*a* on the X2 direction side. The BF separator 22 then collects the complex which includes the antigen, R1 reagent, R2 reagent, and R3 reagent within the cuvette C via magnetic force, and removes the unreacted R3 reagent.

In step S11, the first cuvette transporting part 4 moves the cuvette C from the BF separator 22 to the relay part 14, and sets the cuvette C in the cuvette retaining hole 14*a*.

In step S12, the R4 reagent and R5 reagent are dispensed. The second cuvette transporting part 5 first takes up the cuvette C from the relay part 14, and moves the cuvette C to the R4/R5 reagent dispenser 23. The R4 reagent nozzle 23*a* then dispenses the R4 reagent into the cuvette C while the second cuvette transporting part 5 holds the cuvette C at a position below the R4 reagent nozzle 23*a*. The R5 reagent nozzle 23*b* then dispenses the R5 reagent into the cuvette C while the second cuvette transporting part 5 holds the cuvette C at a position below the R5 reagent nozzle 23*b*.

In step S13, the second cuvette transporting part 5 sets the cuvette C in the cuvette retaining hole 21*d* of the third reactor 21*c*. In this condition, the sample and R1 through R5 reagents within the cuvette C is subjected to a fourth order reaction process by heating to a predetermined temperature for a predetermined time. The process of preparing the measurement sample is completed with the fourth order reaction process.

In step S14, the second cuvette transporting part 5 takes up the cuvette C from the third reactor 21*c*, and sets the cuvette C in the interstage transporting part 15. The elevator device 16 lowers the interstage transporting part 15, and moves the cuvette C to the second stage E2 (refer to FIG. 2).

Optical detection is performed in step S15. Specifically, the third cuvette transporting part 45 takes up the cuvette C from the interstage transporting part 15, and moves the cuvette C to the detector 24, as shown in FIG. 2. The amount of antigen contained in the sample is measured by the optical detector 24*a* of the detector 24. After optical detection is completed, the third cuvette transporting part 45 takes up the measured cuvette C from the detector 24, and sets the cuvette C in the cuvette disposal port 46 in step S16. The measurement process is completed by the analyzer 100 in this manner.

The operation of relaying the cuvette C through the relay part 14 between the first cuvette transporting part 4 and the second cuvette transporting part 5 is described in detail below referring to FIG. 6.

Figure 6:
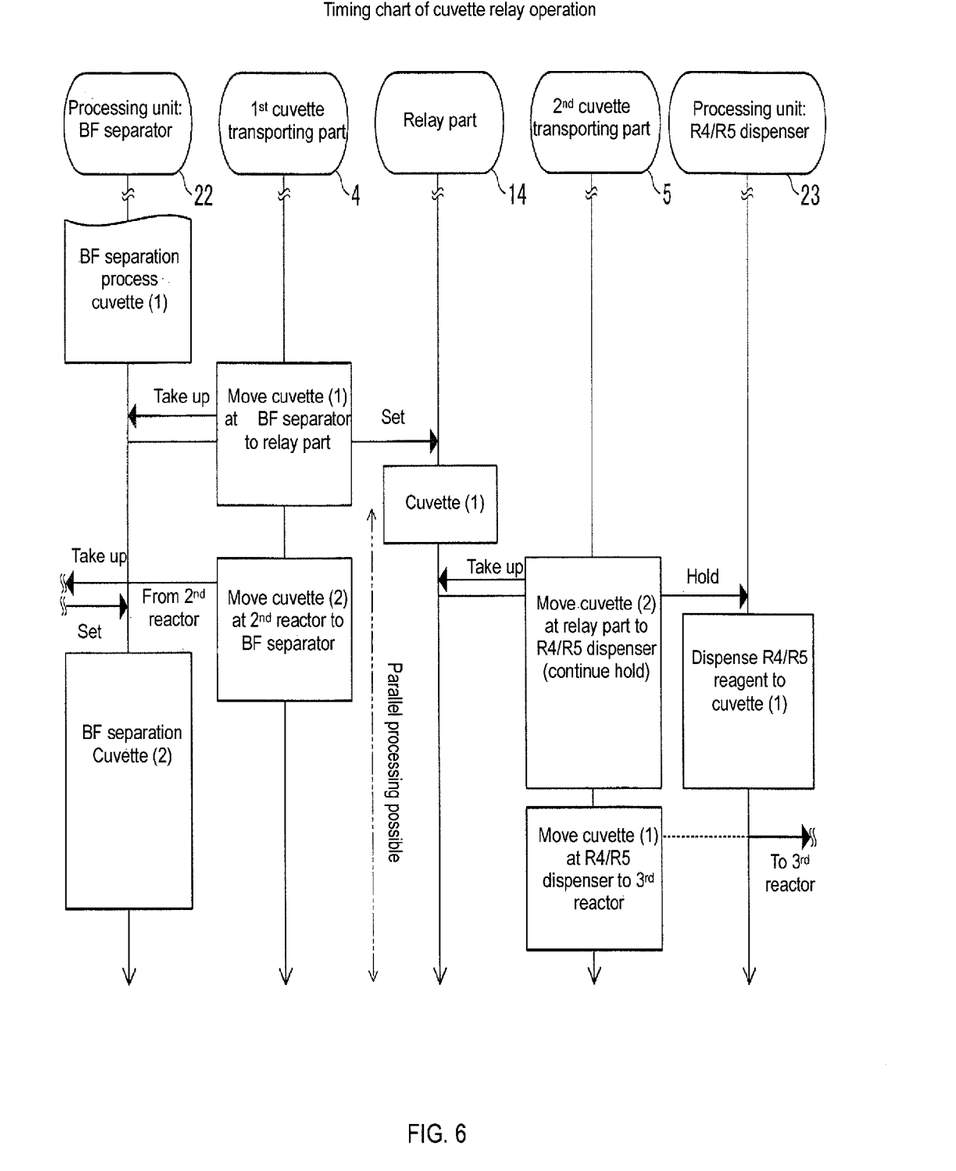
FIG. 6 is a timing chart illustrating the cuvette relay operation of the first cuvette transporting part and the second cuvette transporting part.

As shown in FIG. 6, after the second order BF separation process is completed for a first cuvette C, the first cuvette transporting part 4 takes up the first cuvette C from the processing port 22*a* of the BF separator 22, and moves the first cuvette C to the relay part 14 (refer to step S11 of FIG. 5). In this way the transport operation of the first cuvette C by the first cuvette transporting part 4 ends, and the subsequent processing of the first cuvette C is not restricted by the first cuvette transporting part 4. The first cuvette transporting part 4 executes the transport operation of two subsequent cuvettes C in parallel processes following step S12 of FIG. 5.

That is, regarding the first cuvette C, the second cuvette transporting part 5 takes up the first cuvette C from the relay part 14 and moves the first cuvette C to the R4/R5 reagent dispenser 23, and after the R4 reagent and R5 reagent have been dispensed moves the first cuvette C to the third reactor 21*c*. The second cuvette transporting part 5 continues to hold the cuvette C after picking up the cuvette C from the relay part 14 until moving the cuvette C to the third reactor 21*c*.

In parallel with the operation of the second cuvette transporting part 5, the first cuvette transporting part 4 moves the second cuvette set in the second reactor 21*b* through the magnet port 44 to the BF separator 22. The second cuvette C is then set in the empty processing port 22*a* from which the first cuvette C was previously removed. Therefore, the R4/R5 reagent dispensing process and BF separation process are performed in parallel, and in parallel with the transport operation of the cuvette C to the BF separator 22 on the first cuvette transporting part 4 side even during the operation of the second cuvette transporting part 5 for the R4 and R5 reagent dispensing process.

The following effects are obtained in the present embodiment.

The analyzer 100 has the first cuvette transporting part 4 for moving the cuvette C disposed along the first side 1*a* of the housing 1 on the periphery of the reagent holding part 3, and the second cuvette transporting part 5 for moving the cuvette C disposed along the second side 1*b* of the housing 1 on the periphery of the reagent holding part 3, as described above. The analyzer 100 also has a plurality of processing units 2 respectively arranged in either a direction (first direction X) extending along the first side 1*a* or a direction (second direction Y) extending along the second side 1*b* in planar view, and configured to receive a cuvette C which is moved by the first cuvette transporting part 4 or the second cuvette transporting part 5, and perform predetermined processing of the sample contained in the received cuvette C. The analyzer 100 has the first cuvette transporting part 4 and the second cuvette transporting part 5 disposed along the first side 1*a* and the second side 1*b* of the housing 1, and has a plurality of processing units 2 arranged along the first direction X and the second direction Y. As a result, dead space between the processing units 2 is eliminated, unlike configurations in which the processing units are arranged along the circumference of an annular turntable used to move the cuvettes. Moreover, even when an annular reagent holder 3 is provided, the plurality of processing units 2 need not be arranged around the circumference of the reagent holder 3 by providing the first cuvette transporting part 4 and the second cuvette transporting part 5 respectively along the first side 1*a* and second side 1*b*. The processing units 2 therefore may be arranged in an optional layout so as to reduce as much as possible the dead space between the processing units 2. As a result, the analyzer 100 of the present embodiment can be rendered more compactly, thereby reducing the required installation area.

As described above, the analyzer 100 also has a relay part 14 configured to hold the cuvette C, and which is disposed in the overlap area B of the transport region A1 of the first cuvette transporting part 4 and the transporting region A2 of the second cuvette transporting part 5. Therefore, the cuvette C can pass through the relay part 14 between the first cuvette transporting part 4 and the second cuvette transporting part 5. As a result, the first cuvette transporting part 4 and the second cuvette transporting part 5 can transport the cuvettes C in simultaneous and parallel operations without restricting their mutual operations.

The first cuvette transporting part 4 also is configured to move the cuvette C to the relay part 14 after processing is completed by the processing units 2 arranged along the first side 1a. The second cuvette transporting part 5 is configured to move the cuvette C in the relay part 14 to the processing unit 2 arranged along the second side 1b. Accordingly, the sample contained in the cuvette C can be smoothly processed in the series of processes performed by the processing units 2 even when a plurality of cuvette transporting parts are provided. That is, the cuvette C can be smoothly transported without providing standby time during the transport operations of the first cuvette transporting part 4 and the second cuvette transporting part 5 since the cuvette C moved by the relay part 14 may be taken up from the relay part 14 by the second cuvette transporting part 5 while the next cuvette C is moved by the first cuvette transporting part 4.

As described above, the first cuvette transporting part 4 is configured to reciprocatingly move the first holder 4a in the first direction X. The second cuvette transporting part 5 is configured to reciprocatingly move the first holder 4a in the second direction Y. Accordingly, the same processing unit 2 can be used a plurality of times by the back and forth movement of the first cuvette transporting part 4 and the second cuvette transporting part 5. As a result, the analyzer 100 can be made even more compact since there is no need to install several identical processing units 2 in contrast to with providing a plurality of identical processing units in a structure in which an annular turntable moves a cuvette in one direction to perform the same process several times.

As described above, the first cuvette transporting part 4 is configured so that the range of movement of the first holder 4a in the first direction X is greater than the range of movement in the second direction Y. The second cuvette transporting part 5 is configured so that the range of movement of the second holder 5a in the second direction Y is greater than the range of movement in the first direction X. According to this configuration, the ranges of movement of the first cuvette transporting part 4 and the second cuvette transporting part 5 respectively are long and narrow along the first side 1a and the second side 1b. The increase in space accordingly is avoided between the annular reagent holding part 3 and the first side 1a and second side 1b, and a wide space is ensured in the longitudinal direction of the movement range. As a result, an increase in the installation area of the analyzer 100 is prevented, thus improving the freedom in the layout of the plurality of processing units 2.

As described above, the transport positions of the cuvette C to the processing units 2 disposed along the first side 1a are arranged so as to be within the movement range of the first holder 4a. The transport positions of the cuvette C to the processing units 2 disposed along the second side 1b also are arranged so as to be within the movement range of the second holder 5a. According to this configuration, the first cuvette transporting part 4 and the second cuvette transporting part 5 directly transport the cuvette C to the processing units 2 respectively along the first side 1a and the second side 1b. Since it is therefore unnecessary to provide a separate transporter to relay the cuvette C between the first cuvette transporting part 4 and the second cuvette transporting part 5, and the processing units 2, the installation area of the analyzer 100 is not increased, and the cuvette C can be efficiently and reliably transported.

In the analyzer 100 described above, reactor 21, which holds the cuvette C and induces the reaction of the sample in the cuvette C, is provided as one of the plurality of processing units 2. In this way the apparatus can be made compactly since reactors 21 of sufficient size can be arranged along the first side 1a and second side 1b of the housing 1, unlike a configuration in which large annular reactors are provided.

As described above, the reagent holding part 3 internally houses and cools the reagent container, and is arranged near the center of the housing 1 in the planar view. The reactors 22 and 23 which heat the sample contained in the cuvette C are arranged at positions separated from the reagent holding part 3 within the cuvette C transport region A1 or A2 of the first cuvette transporting part 4 and second cuvette transporting part 5, respectively. In this way the installation area can be reduced to render the analyzer more compact, and a layout which improves thermal energy efficiency can be realized by separating the relatively high temperature of the reactors 22 and 23 from the relatively low temperature of the reagent holding part 3.

As described above, the analyzer 100 provides, as one of the plurality of processing units 2, a BF separator 22 which separates the unreacted component in the sample contained in the cuvette C, and is arranged at a position between the second reactor 21b and the third reactor 21c. In this way the transport distance of the cuvette C is reduced between the BF separator 22, and the second reactor 21b and third reactor 21c, and processing is performed efficiently when performing the separation process to separate the unreacted component after the reaction in the second reactor 21b, and the reaction process in the third reactor 21c following the separation process.

The sample dispensing cuvette mover 10 includes the sample dispensing cuvette holder 10a to retain the cuvette C, and is provided along the second direction Y so that the sample dispensing cuvette holder can move reciprocatingly in the second direction Y. Since the dead space within the analyzer is thereby further reduced, the analyzer is rendered more compact.

The sample dispensing cuvette mover 10 is configured to move the cuvette C held in the sample dispensing cuvette holder between the sample dispensing position P1 where sample is dispensed, the reagent dispensing position P2 where R1 reagent is dispensed, and cuvette removal position P3 where the cuvette containing the dispensed sample and reagent is taken up. Hence, sample dispensing and reagent dispensing can be performed rapidly.

The plurality of processing units 2 and the sample dispensing cuvette mover 10 are provided around the annular reagent holding part 3. In this way the analyzer can be made even more compact by removing the dead space between the reagent holding part 3, and the plurality of processing units 2 and the sample dispensing cuvette mover 10.

The dead space within the housing 1 is more effectively reduced because the housing 1 has a rectangular shape in planar view.

The first stage E1 and the second stage E2 are provided one above the other in the analyzer 100 described above. The processing units 2 arranged in the second stage E2 of the housing 1 differ from the processing units 2 arranged along the first side 1a of the first stage E1 and the processing units 2 arranged along the second side 1b of the first stage E1. Therefore, the installation area of the analyzer is rendered even smaller compared to configurations in which, for example, all processing units are arranged in a planar manner in a single stage.

As described above, the analyzer 100 is further provided with an interstage transporting part 15, and an elevator device 16 to lift and lower the interstage transporting part 15. In this way the installation area of the analyzer is made smaller because, for example, the first cuvette transporting part 4 and the second cuvette transporting part 5 are not required to be provided so as to span the first stage E1 and the second stage E2 since the cuvette C can be moved between the first stage E1 and the second stage E2 by the interstage transporting part 15.

The analyzer 100 is an immunoanalyzer as mentioned above. In this way the analyzer can be made more compact and the installation area can be reduced even in the case of an immunoanalyzer provided with several processing units to perform many processes.

Note that the embodiment of the present disclosure is an example in all aspects and not to be considered limiting in any way. The scope of the present invention is expressed by the scope of the claims and not by the description of the embodiment, and includes all meanings and equivalences and modifications pertaining thereunto.

For example, although the above embodiment is described by way of example in which the present invention is applied to an immunoanalyzer for measuring antibodies or antigen contained in a sample to be measured, the present invention is not limited to this example. The present invention also may be applied to other analyzers which are not immunoanalyzers. For example, the present invention is applicable to other clinical sample analyzers such as blood coagulation measuring apparatus, urine component analyzer, gene amplification measuring apparatus, and biological analyzer and the like.

What is claimed is:

1. An analyzer comprising:
a housing which has a mutually adjacent first side and a second side;
an annular reagent holding part provided within the housing;
a first cuvette transporting part configured to move a cuvette, provided along the first side on the periphery of the reagent holding part in the housing;
a second cuvette transporting part configured to move a cuvette, provided along the second side on the periphery of the reagent holding part in the housing; and
a plurality of processing units respectively arranged in the housing, and configured to receive a cuvette which is moved from the first cuvette transporting part or the second cuvette transporting part, and perform predetermined processing of the sample contained in the received cuvette,
wherein the first cuvette transporting part and the second cuvette transporting part are configured to have partially overlapping cuvette transport regions in planar view, and
the analyzer further comprises a relay part, configured to hold a cuvette, and arranged in the overlapping part of the transport region of the first cuvette transporting part and the transport region of the second cuvette transporting part.

2. The analyzer of claim 1, wherein
the first cuvette transporting part is configured to move a cuvette which has completed processing by the processing units arranged along the first side to the relay part; and
the second cuvette transporting part is configured to move the cuvette which has been moved by the relay part to the processing units arranged along the second side.

3. The analyzer of claim 1, wherein
the first cuvette transporting part comprises a first holding part capable of holding a cuvette, and is configured to reciprocatingly move the first holding part in a first direction extending along the first side; and
the second cuvette transporting part comprises a second holding part capable of holding a cuvette, and is configured to reciprocatingly move the second holding part in a second direction extending along the second side.

4. An analyzer comprising:
a housing which has a mutually adjacent first side and a second side;
an annular reagent holding part provided within the housing;
a first cuvette transporting part configured to move a cuvette, provided along the first side on the periphery of the reagent holding part in the housing;
a second cuvette transporting part configured to move a cuvette, provided along the second side on the periphery of the reagent holding part in the housing; and
a plurality of processing units respectively arranged in the housing, and configured to receive a cuvette which is moved from the first cuvette transporting part or the second cuvette transporting part, and perform predetermined processing of the sample contained in the received cuvette, wherein
the first cuvette transporting part comprises a first holding part capable of holding a cuvette, and is configured to reciprocatingly move the first holding part in a first direction extending along the first side,
the second cuvette transporting part comprises a second holding part capable of holding a cuvette, and is configured to reciprocatingly move the second holding part in a second direction extending along the second side,
the first cuvette transporting part is configured to reciprocatingly move the first holding part in the first direction and the second direction, and the movement range of the first holding part in the first direction is greater than the movement range in the second direction, and
the second cuvette transporting part is configured to reciprocatingly move the second holding part in the second direction and the first direction, and the movement range of the second holding part in the second direction is greater than the movement range in the first direction.

5. The analyzer of claim 4, wherein
a transport position of the cuvette to be transported by the first cuvette transporting part is disposed within a movement range of the first holding part; and
a transport position of the cuvette to be transported by the second cuvette transporting part is disposed within a movement range of the second holding part.

6. The analyzer of claim 1, wherein
at least one of the plurality of processing units is a reaction unit having a plurality of cuvette retaining holes each configured to hold a cuvette, the reaction unit reacting a sample contained in the cuvette.

7. An analyzer comprising:
a housing which has a mutually adjacent first side and a second side;
an annular reagent holding part provided within the housing;

a first cuvette transporting part configured to move a cuvette, provided along the first side on the periphery of the reagent holding part in the housing;
a second cuvette transporting part configured to move a cuvette, provided along the second side on the periphery of the reagent holding part in the housing; and
a plurality of processing units respectively arranged in the housing, and configured to receive a cuvette which is moved from the first cuvette transporting part or the second cuvette transporting part, and perform predetermined processing of the sample contained in the received cuvette, wherein
at least one of the plurality of processing units is a reaction unit having a plurality of cuvette retaining holes each configured to hold a cuvette, the reaction unit reacting a sample contained in the cuvette,
the reagent holding part is configured to internally accommodate and cool reagent containers, and is arranged near the center of the housing in planar view, and
the reaction unit is configured to heat the sample contained in the cuvette, and is arranged within the cuvette movement range of the first cuvette transporting part or the second cuvette transporting part, that is, at a position separated from the reagent holding part.

8. An analyzer comprising:
a housing which has a mutually adjacent first side and a second side;
an annular reagent holding part provided within the housing;
a first cuvette transporting part configured to move a cuvette, provided along the first side on the periphery of the reagent holding part in the housing;
a second cuvette transporting part configured to move a cuvette, provided along the second side on the periphery of the reagent holding part in the housing; and
a plurality of processing units respectively arranged in the housing, and configured to receive a cuvette which is moved from the first cuvette transporting part or the second cuvette transporting part, and perform predetermined processing of the sample contained in the received cuvette, wherein
at least one of the plurality of processing units is a reaction unit having a plurality of cuvette retaining holes each configured to hold a cuvette, the reaction unit reacting a sample contained in the cuvette,
a plurality of the reaction units are provided, and
at least one of the plurality of processing units is a BF separator configured to separate unreacted components in the sample contained in the cuvette, and is arranged at a position between the plurality of the reaction units.

9. An analyzer comprising:
a housing which has a mutually adjacent first side and a second side;
an annular reagent holding part provided within the housing;
a first cuvette transporting part configured to move a cuvette, provided along the first side on the periphery of the reagent holding part in the housing;
a second cuvette transporting part configured to move a cuvette, provided along the second side on the periphery of the reagent holding part in the housing; and
a plurality of processing units respectively arranged in the housing, and configured to receive a cuvette which is moved from the first cuvette transporting part or the second cuvette transporting part, and perform predetermined processing of the sample contained in the received cuvette, wherein the first cuvette transporting part comprises a first holding part capable of holding a cuvette, and is configured to reciprocatingly move the first holding part in a first direction extending along the first side; and
the second cuvette transporting part comprises a second holding part capable of holding a cuvette, and is configured to reciprocatingly move the second holding part in a second direction extending along the second side, and
the analyzer further comprises:
a sample dispensing cuvette transporting part provided along the first direction or the second direction, which has a sample dispensing cuvette holder capable of holding a cuvette; and which is configured to reciprocatingly move the sample dispensing cuvette holder in the first direction or the second direction.

10. The analyzer of claim 9, wherein
the sample dispensing cuvette transporting part is configured to move the cuvette held in the sample dispensing cuvette holder between a sample dispensing position for dispensing a sample, and a cuvette removal position for removing the cuvette which contains dispensed sample and reagent.

11. The analyzer of claim 9, wherein
the plurality of processing units and the sample dispensing cuvette transporting part are provided around the annular reagent holder.

12. The analyzer of claim 1, wherein
the housing is configured in a rectangular shape in planar view.

13. An analyzer comprising:
a housing which has a mutually adjacent first side and a second side;
an annular reagent holding part provided within the housing;
a first cuvette transporting part configured to move a cuvette, provided along the first side on the periphery of the reagent holding part in the housing;
a second cuvette transporting part configured to move a cuvette, provided along the second side on the periphery of the reagent holding part in the housing; and
a plurality of processing units respectively arranged in the housing, and configured to receive a cuvette which is moved from the first cuvette transporting part or the second cuvette transporting part, and perform predetermined processing of the sample contained in the received cuvette, wherein
the housing is configured by the first cuvette transporting part and second cuvette transporting part, a first stage with an arrangement of the plurality of processing units, and a second stage which differs from the first stage in a vertical direction, and
the second stage has an arrangement of a processing unit which are different from the processing unit arranged along the first side and the processing unit arranged along the second side.

14. The analyzer of claim 13, further comprising:
an interstage transporting part configured to hold a cuvette; and
an elevator device configured to move a cuvette between the first stage and the second stage by lifting and lowering the interstage transporting part.

15. The analyzer of claim 1, wherein
the analyzer is an immunological analyzer.

* * * * *

UNITED STATES PATENT AND TRADEMARK OFFICE
CERTIFICATE OF CORRECTION

PATENT NO. : 9,874,511 B2  
APPLICATION NO. : 14/669801  
DATED : January 23, 2018  
INVENTOR(S) : Toshikatsu Fukuju et al.

Page 1 of 1

It is certified that error appears in the above-identified patent and that said Letters Patent is hereby corrected as shown below:

In the Claims

In Column 16, Claim 5, Line 49, replace "claim 4" with --claim 3--.

Signed and Sealed this  
Twenty-first Day of August, 2018

Andrei Iancu  
*Director of the United States Patent and Trademark Office*